US008639306B2

(12) United States Patent
Cornsweet

(10) Patent No.: US 8,639,306 B2
(45) Date of Patent: Jan. 28, 2014

(54) NONINVASIVE EYE-PROPERTY MONITORING, INCLUDING AQUEOUS-HUMOR GLUCOSE MONITORING AS AN INDICATION OF BLOOD GLUCOSE LEVEL

(75) Inventor: Tom N. Cornsweet, Prescott, AZ (US)

(73) Assignee: Brien Holden Vision Diagnostics, Inc., Prescott, AZ (US)

( * ) Notice: Subject to any disclaimer, the term of this patent is extended or adjusted under 35 U.S.C. 154(b) by 169 days.

(21) Appl. No.: 13/366,299

(22) Filed: Feb. 4, 2012

(65) Prior Publication Data
US 2012/0215079 A1 Aug. 23, 2012

Related U.S. Application Data

(60) Provisional application No. 61/462,677, filed on Feb. 7, 2011.

(51) Int. Cl.
A61B 5/1455 (2006.01)

(52) U.S. Cl.
USPC .......................................... 600/319; 600/318

(58) Field of Classification Search
USPC .................................. 600/310, 316, 318, 319
See application file for complete search history.

(56) References Cited

U.S. PATENT DOCUMENTS

| 3,536,383 | A | 10/1970 | Cornsweet et al. |
| 3,582,775 | A | 6/1971 | Cornsweet |
| 3,614,214 | A | 10/1971 | Cornsweet |
| 3,639,041 | A | 2/1972 | Cornsweet |
| 3,693,019 | A | 9/1972 | Grenda et al. |
| 3,712,716 | A | 1/1973 | Cornsweet et al. |
| 3,723,648 | A | 3/1973 | Cornsweet |
| 3,724,932 | A | 4/1973 | Cornsweet et al. |
| 3,804,496 | A | 4/1974 | Cornsweet et al. |
| 3,819,256 | A | 6/1974 | Bellows et al. |
| 3,832,066 | A | 8/1974 | Cornsweet |
| 3,843,240 | A | 10/1974 | Cornsweet |
| 3,864,030 | A | 2/1975 | Cornsweet |
| 3,870,415 | A | 3/1975 | Cornsweet |
| 3,958,560 | A * | 5/1976 | March .......................... 600/319 |
| 3,963,019 | A | 6/1976 | Quandt |
| 4,019,813 | A | 4/1977 | Cornsweet et al. |
| 4,169,676 | A * | 10/1979 | Kaiser .......................... 600/322 |
| 4,281,926 | A | 8/1981 | Cornsweet |
| 4,329,049 | A | 5/1982 | Rigg et al. |
| 4,704,029 | A * | 11/1987 | Van Heuvelen ............... 600/316 |
| 4,715,703 | A | 12/1987 | Cornsweet et al. |
| 4,819,752 | A | 4/1989 | Zelin |
| 5,042,937 | A | 8/1991 | Cornsweet |
| 5,114,222 | A | 5/1992 | Cornsweet |
| 5,196,872 | A | 3/1993 | Beesmer et al. |
| 5,210,554 | A | 5/1993 | Cornsweet et al. |

(Continued)

Primary Examiner — Eric Winakur
(74) Attorney, Agent, or Firm — Jones Day

(57) ABSTRACT

An eye-property monitoring system and method for performing the steps of (1) illuminating the eye from at least one light source whose wavelength interacts with internal eye properties in an optically active manner, (2) controlling, to make known and stable, the operating-power/light-output level of the source, (3) by such illuminating, producing light-source eye reflections including (a) multiple internal reflections within the outer structure of the eye, and (b) linked with those internal reflections at least one resulting outbound reflection, (4) monitoring the outbound-reflection to detect therein the reflection level associated with the at least one source, and (5) associating such detected reflection level as an indication of certain eye properties, such as aqueous glucose concentration.

24 Claims, 1 Drawing Sheet

(56) References Cited

U.S. PATENT DOCUMENTS

| | | | |
|---|---|---|---|
| 5,410,376 | A | 4/1995 | Cornsweet et al. |
| 5,422,690 | A | 6/1995 | Rothberg et al. |
| 5,535,743 | A | 7/1996 | Backhaus et al. |
| 5,560,356 | A | 10/1996 | Peyman |
| 5,820,557 | A | 10/1998 | Hattori et al. |
| 5,961,449 | A | 10/1999 | Toida et al. |
| 5,969,815 | A | 10/1999 | Toida et al. |
| 6,082,858 | A | 7/2000 | Grace et al. |
| 6,128,091 | A * | 10/2000 | Uchida et al. .......... 356/432 |
| 6,152,875 | A | 11/2000 | Hakamata |
| 6,226,089 | B1 * | 5/2001 | Hakamata ............. 600/319 |
| 6,296,358 | B1 | 10/2001 | Cornsweet et al. |
| 6,424,849 | B1 * | 7/2002 | Berman et al. ......... 600/316 |
| 6,424,850 | B1 | 7/2002 | Lambert et al. |
| 6,659,613 | B2 | 12/2003 | Applegate et al. |
| 6,704,588 | B2 * | 3/2004 | Ansari et al. ........... 600/319 |
| 6,789,900 | B2 | 9/2004 | Van de Velde |
| 6,830,336 | B2 | 12/2004 | Fransen |
| 6,834,958 | B2 | 12/2004 | Cornsweet et al. |
| 6,836,337 | B2 | 12/2004 | Cornsweet |
| 6,885,882 | B2 | 4/2005 | Cote et al. |
| 7,025,459 | B2 | 4/2006 | Cornsweet et al. |
| 7,077,521 | B2 | 7/2006 | Thomas |
| 7,118,217 | B2 | 10/2006 | Kardon et al. |
| 7,156,518 | B2 | 1/2007 | Cornsweet et al. |
| 7,167,736 | B2 | 1/2007 | Winther |
| 7,360,895 | B2 | 4/2008 | Cornsweet et al. |
| 7,470,025 | B2 | 12/2008 | Iwanaga |
| 7,896,496 | B2 | 3/2011 | Hammer et al. |
| 7,896,498 | B2 | 3/2011 | Munger et al. |
| 2004/0046935 | A1 | 3/2004 | Copland |
| 2004/0138539 | A1 | 7/2004 | Jay et al. |
| 2004/0189937 | A1 | 9/2004 | Okinishi |
| 2004/0263784 | A1 | 12/2004 | Cornsweet et al. |
| 2005/0070772 | A1 | 3/2005 | Cornsweet |
| 2005/0124869 | A1 | 6/2005 | Hefti et al. |
| 2005/0143662 | A1 | 6/2005 | Marchitto et al. |
| 2005/0171413 | A1 | 8/2005 | Blair |
| 2005/0187443 | A1 | 8/2005 | Routt et al. |
| 2006/0184040 | A1 | 8/2006 | Keller et al. |
| 2007/0091265 | A1 | 4/2007 | Kardon et al. |
| 2008/0231803 | A1 | 9/2008 | Feldon et al. |
| 2008/0249381 | A1 | 10/2008 | Muller et al. |
| 2009/0116214 | A1 | 5/2009 | Phillips, III et al. |
| 2009/0201490 | A1 | 8/2009 | Gerlitz |
| 2010/0152558 | A1 | 6/2010 | Gerlitz |
| 2010/0201944 | A1 | 8/2010 | Lewis et al. |
| 2010/0277692 | A1 | 11/2010 | Mukai et al. |
| 2011/0105858 | A1 | 5/2011 | Cho et al. |
| 2011/0184261 | A1 | 7/2011 | Menon |

* cited by examiner

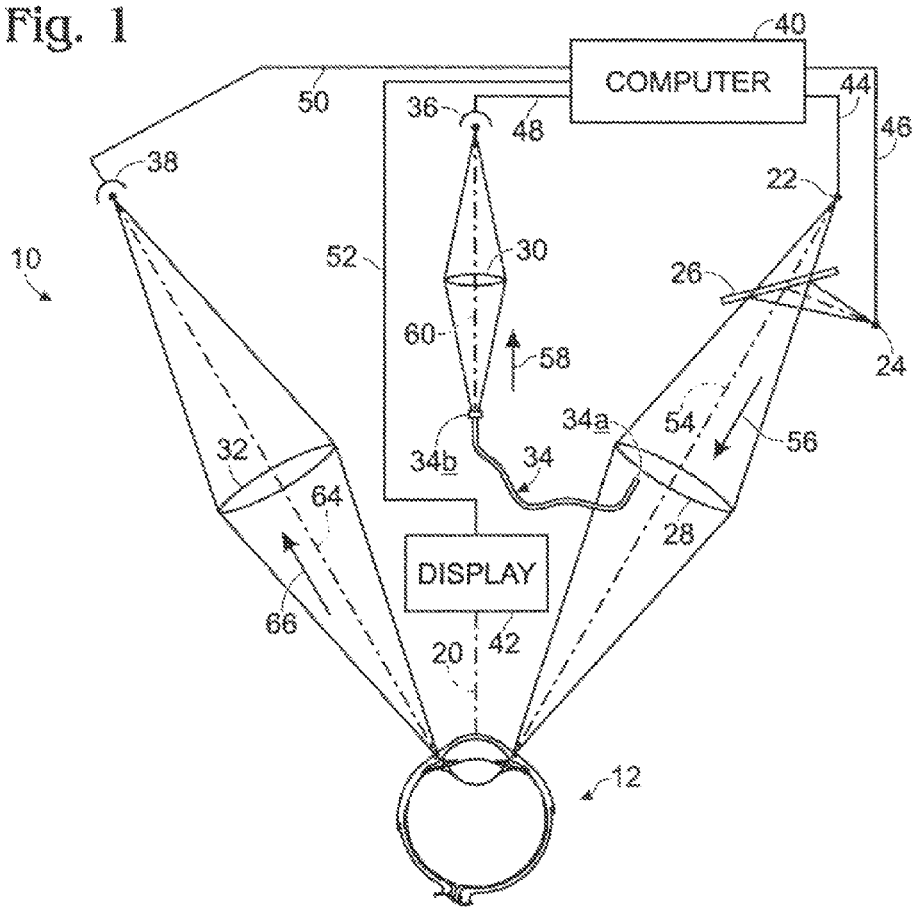
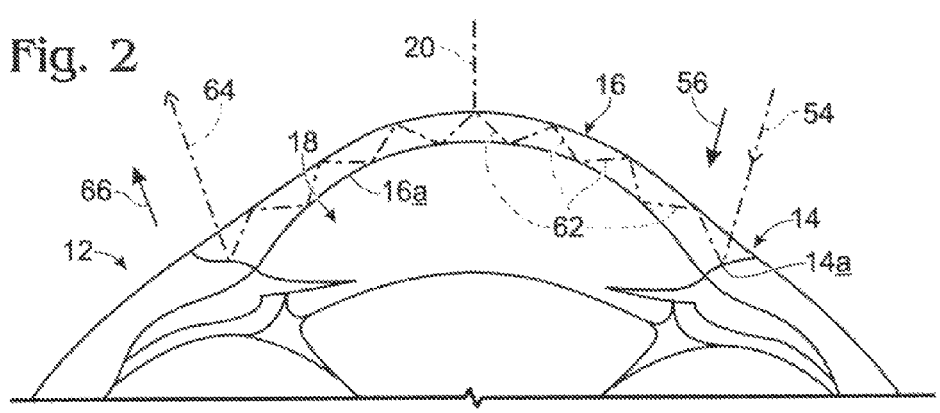

NONINVASIVE EYE-PROPERTY MONITORING, INCLUDING AQUEOUS-HUMOR GLUCOSE MONITORING AS AN INDICATION OF BLOOD GLUCOSE LEVEL

CROSS REFERENCE TO RELATED APPLICATION

This application claims filing-date priority to currently U.S. Provisional Patent Application Ser. No. 61/462,677, filed Feb. 7, 2011, for "Non-invasive Aqueous Humor Glucose Monitor", the entire disclosure content in which is hereby incorporated herein by reference.

BACKGROUND AND SUMMARY OF THE INVENTION

The present invention pertains to noninvasive eye-property monitoring, and more particularly to the noninvasive monitoring of various eye properties through noting how, in an observed light reflection from the eye, certain characteristics of selected and controlled light which has been directed toward the eye have become affected in the process of the directed light's engagement with the eye. While there are many useful applications for the practice of this invention, I have found that its methodology offers particular, and notably high, utility in relation to the monitoring of aqueous-humor glucose content as an indication of blood glucose level— an important, medically-associated diagnostic task. Consequently, while practice of the invention involves the broader concept of using specially created and controlled eye-directed, and resulting eye-reflected, light in the practice of looking at various eye properties, both for assessing these properties as end results in and of themselves, and additionally for using these detected properties as related indicators of other physical conditions, a preferred and best-mode system for, and manner of, practicing the invention are illustrated and described herein specifically in the mentioned high-utility setting of glucose monitoring through examining how the presence of glucose in the aqueous humor (the aqueous) effects certain interactions with certain characters of light. Such effecting results from what is referred to herein as optical activity, and an illustration of optical activity is a change in qualities of light reflection from the eye.

Other, representative (non-exhaustive) eye "properties" associated with the aqueous humor, known to be of interest, and regarding which the invention may be employed, include uric acid, ascorbate, lactic acid, inorganic phosphates, bicarbonates, chlorides, and urea.

Moving along now, and considering the topic of glucose, maintaining an appropriate concentration of glucose in the blood is critical for reducing the likelihood of complications from diabetes mellitus. Currently, blood glucose concentration is usually measured by extracting a drop of blood and subjecting it to a form of chemical analysis.

It would obviously be preferable to be able to measure blood glucose concentration non-invasively. However; many constituents of blood and skin other than glucose have so far prevented the successful development of an instrument to measure blood glucose through the skin.

There is good evidence that the concentration of glucose in the aqueous humor of the eye varies with blood glucose concentration, with a lag of about ten minutes. Further, the aqueous humor contains far fewer confounding components than does blood, and it lies behind transparent tissue, the cornea, instead of being shielded by skin. Therefore, attempting to measure glucose concentration in the aqueous, as I have found, has promise for providing a non-invasive measure of blood glucose level.

When the glucose concentration in the aqueous changes, the index of refraction of the aqueous changes proportionately. Further, the amount of change in the index is different for different wavelengths of light. When light is reflected from an interface between two partially transparent substances, the proportion of incident light that is reflected depends upon the ratio of the indices of refraction of the two substances. Therefore, if the glucose concentration in the aqueous changes, the intensity of light reflected from the interface between the back surface of the cornea and the aqueous will change, and the change will be different for different wavelengths.

Regarding another useful phenomenon, when light passes through the aqueous humor, an amount of it is absorbed that depends upon the wavelength of the light involved, and the amount of glucose in the aqueous humor.

As will be seen, the system and methodology of the present invention, in the illustrative glucose-detection/monitoring setting described below, produce information contained in light-associated, optical-activity-affected, reflected light which furnishes a measure of aqueous glucose concentration— which information may be based upon either changes in index of refraction or of absorption or both. With appropriate calibration, it makes no difference which, or whether both, of these two optical phenomena contribute to this information. Such calibration may be performed by conducting a conventional blood glucose concentration test, and then, essentially at the same time, implementing eye-reflection-condition monitoring in accordance with the invention to compare data.

According to one way of expressing the invention, based upon considering the invention in its broader aspects, what is proposed is an eye-property monitoring system and methodology collectively featuring the enabling and practicing of the steps including (1) illuminating the eye from at least one light source whose wavelength interacts with internal eye properties in an optically active manner, (2) controlling, to make substantially known and stable, at a predetermined setting, the operating power/light-output level of the source, (3) by such illuminating, producing light-source eye reflections including (a) multiple internal reflections within the outer structure of the eye, and (b) at least one resulting outbound reflection, (4) monitoring the outbound-reflection to detect therein the reflection level associated with the at least one source, and (5) associating such detected reflection level as an indication of certain eye properties.

According to another, currently preferred and best-mode manner of practicing the invention, based upon the features and operation of the disclosed system of the invention, what is proposed is an eye-property monitoring method including (a) in a seriatim manner, illuminating the eye (one or more region(s) on the limbus) from two or more, different-wavelength light sources whose respective wavelengths interact with internal eye properties in optically differentiated manners, (b) adjusting the operating levels of the sources to a predetermined relative setting, (c) by such illuminating, producing seriatim-light-source eye reflections including multiple internal reflections within the outer structure of the eye, and at least one resulting outbound reflection, (d) monitoring the outbound-reflection to detect therein the relative reflection levels associated with the sources, and (e) associating such detected, relative reflection levels as an indication of certain eye properties.

According to still another, alternative, preferred and best-mode manner of practicing the invention utilizing its system, which manner expresses the invention in a more specific sense, proposed is a blood glucose monitoring method including (a) in an alternating manner, illuminating the eye (again, one or more region(s) on the limbus) from two, different-wavelength light sources, one of which has a wavelength to which glucose is more optically active than it is to the wavelength of the other source, (b) adjusting the operating levels of the two sources to a predetermined relative setting, (c) by such illuminating, producing eye reflections including multiple internal reflections within the outer structure of the eye, and at least one resulting outbound reflection, and (d) monitoring a selected condition of the outbound reflection as an indication of blood glucose level.

Even more specifically, the system-implementable methodology of the invention, as expressed in all three of the ways stated above, is preferably computer-based, and includes both (1) computer controlling of the illuminating, controlling and adjusting steps, and (2) computer conducting of the monitoring step. Illuminating is performed by directing light from the employed light sources along a common (in the case of two or more sources) illumination path which lies at an angle relative to the eye's line of sight, and the producing step is accomplished to effect eye reflections occurring within the cornea of the eye, and even more particularly is conducted so as to effect eye reflections, including multiple reflections, from the optical interface existing between the cornea (its inside, or back surface, or side) and the aqueous humor of the eye.

In thinking about this interface, it is interesting, and useful, to note that the inside surface of the cornea is completely covered, in a healthy eye, with a very thin layer of what are called endothelial cells. These cells may well affect the amount of light reflected at each cornea-reflection "bounce", and so, a result, in terms of quantum mechanics, of such behavior is that photons meeting the inner surface of the cornea at a shallow angle (in a manner producing what is known in the relevant art as total internal reflection) will "tunnel" through the interface, and, if the properties of the endothelial cells are "right" (in a sense known to those skilled in the art), some of the associated light will escape the cornea (a phenomenon known as "frustrated total internal reflection"). Accordingly, if the thickness, or the index of refraction, or both, of the endothelial cells changes with glucose concentration, that will also affect monitoring measurement, and may do so perhaps beneficially, and maybe even strongly. Appropriate implementation-system calibration will take into account this potentially very useful phenomenon.

In the structural environment adjacent these endothelial cells, optical-reflection physics may actually be quite more complex than simple, in the sense that "internal-eye-structure" reflections produced by practice of the invention might include both (a) reflections from the optical interface existing between the cornea and the endothelial cells, and (b) reflections between the endothelial cells and the aqueous. It is also possible, in relation to monitoring glucose, that glucose concentration might affect the properties of the endothelial cells, for example in a manner, such as by cell-layer thickening, affecting reflection intensity. All of these considerations, however, complexities set aside from detailed analysis, will not affect the viability of invention practice with the earlier mentioned system calibration steps taken with respect to each examined person.

As will become evident, the optical, and associated computer-control, system which implements the methodology of the invention may be relatively simple in construction, and can readily lend itself to economical and compact construction—features which those skilled in the art will easily understand. Additionally, those skilled in the art will immediately recognize the possibilities for numerous variations in systemic and detailed methodologic practices that will lie well within the scope of the invention's basic contributions to the art, as expressed very generally above, and these matters testify to the important flexibility and versatility of the invention.

For examples, one can say, generally, about systemic and practice modifications which may readily be implemented by a user seeking to practice the methodology of the present invention in a manner best suited to the application chosen by that user, that they may include the following considerations.

While the system and methodology of the present invention are specifically illustrated and described herein principally in conjunction with the use of two, different-wavelength light sources, one should understand, and those skilled in the art will clearly appreciate, (a) that a greater number than two such sources may be employed, (b) that such sources may be designed to operate at wavelengths which differ from the specific wavelengths that are identified in text below, (c) that it is possible to use only a single wavelength, even with plural sources, if desired, and (d) that there may be applications wherein even only a single light source, operating, of course, at but a single wavelength, may be used. In all instances, it is important that chosen wavelengths, or a single chosen wavelength if that is what is to be employed, interact optically in a "noticeable" manner (as by experiencing changing eye-reflection characteristics) with the selected properties in the eye that are to be monitored so that light-impingement-produced reflection which is received and reviewed, in accordance with practice of the invention, will possess "reflection content" suitably indicative of the specific eye properties which are being examined. Those skilled in the relevant art will clearly appreciate these several matters.

With regard to the situation where plural light sources are employed, and more specifically where more than two such sources are used, the interrelating operations thereof, referred to as "seriatim" operations, may take place in various, user-selected patterns of energization.

Additionally, where plural light sources are used, the flow paths, or lines, along which incident illumination coming respectively from these sources need not exactly match one another, and while incident illumination should always strike a region on the limbus of eye, the incident beams need not necessarily strike exactly the same region of the limbus.

Yet another consideration is that, while the preferred and best-mode implementation of the invention specifically involves incident light being directed at an angle to the line of sight of the eye, it is entirely possible to consider illuminating the eye, and specifically a location on the limbus, along a line of illumination which may even parallel the line of sight. Important here is that light impingement be at a region on the limbus, and not more eye-centrally—a condition which might produce unwanted and interfering reflection(s) from the cornea.

Still a further consideration regarding what one skilled in the art choosing to implement the methodology of the present invention might consider doing involves suitably supporting the optical elements that are pictured and described herein on appropriate motor-driven support structure, under the control of the illustrated computer, for the purpose of automating precise positioning between these optical elements and a person's eye. There are many ways in which this kind of an arrangement might be made, all well within the conventional skills of those generally skilled in the relevant art, and accordingly, this area of "invention modification" is not specifically illustrated or further described herein.

These and various other features, advantages and possible modifications that characterize the present invention will become more fully apparent as the detailed description of it which follows below is read in conjunction with the accompanying drawings.

DESCRIPTIONS OF THE DRAWINGS

FIG. 1 is a simplified, block/schematic diagram illustrating, in relation to a human eye, not only a preferred and best-mode form of an optical system which is operable to implement and practice the methodology of the present invention, but also, as will be discussed later herein, certain modified forms of the invention, including a single-light-source modification respecting which certain system components illustrated in the figure will effectively be treated as being absent.

FIG. 2 is an enlarged, fragmentary, cross-sectional view of the front portion of the eye shown in FIG. 1, specifically illustrating a representative pathway of a beam of light incident on the front portion of eye, and of resulting internal and outbound reflections which occur in accordance with practice of the invention— the internal reflections taking place within the cornea, and specifically including reflections from the optical interface which exists between the rear surface of the cornea and the aqueous humor.

Various component sizes, and light-beam angles, that are pictured in these two drawing figures are not drawn, or presented, to scale

DETAILED DESCRIPTION OF THE INVENTION

Turning now to the drawings, indicated generally in a downwardly-looking plan view at 10 in FIG. 1 is an integrated optical, computer and electronic system constructed to perform, in a preferred and best-mode manner, the eye-property monitoring methodology of the present invention. System 10 appears is pictured in full operative association with a human eye which is shown at 12. FIG. 2 illustrates, in a greatly enlarged, fragmentary, and cross-sectional manner, the front portion of eye 12 which includes the well-known ring-shaped region 14 (edges only of which are shown) known as the limbus, a structure that essentially surrounds the outwardly convexly-shaped cornea 16. The concavely-shaped inner, or back, surface of cornea 16, indicated at 16a, forms one side of an optical interface with the aqueous humor shown at 18. A representative line-of-sight for eye 12 is shown by a dash-dot line 20 in both drawing figures.

Included in system 10 are two light-emitting-diode (LED) light sources, or light-source structure, 22, 24, an appropriate (regarding light-source wavelengths), conventional optical beam combiner 26, three lenses, shown at 28, 30, 32, an elongate optical fiber 34 having input and output ends 34a, 34b, respectively, two photodiodes, photodetectors, or optical monitoring structure, 36, 38, a suitably algorithmically programmed digital computer, or result-determining structure, 40, and a screen display 42. Appropriate control and data-flow connection lines 44, 46, 48, 50, 52 connect computer 40 to light source 22, light source 24, photodiode 36, photodiode 38, and screen display 42, respectively.

Interposed computer 40 and each of control connection lines 44, 46, but not specifically appearing in FIG. 1, are an appropriate, conventional, upstream, single, digital-to-analogue converter, and downstream from this converter, and intermediate the converter and the mentioned, two control connection lines, a control-connection-line-shared LED switching and operating-current-level controller. The performances of these two, conventional electronic devices (the converter and the controller) which lie between the computer and sources 22, 24 will be explained shortly.

Referring to the two data-flow connection lines which exist, as shown, between the two photodiodes and computer 40, interposed photodiodes 36, 38 and their respectively connected and associated data-flow connection lines 48, 50, and also not specifically illustrated in FIG. 1, is, in each individual case, a series-connected electronic circuitry arrangement including an appropriate, conventional signal amplifier, and between this amplifier and the associated data-flow connection line, a conventional analogue-to-digital converter. How these elements work in the practice of the invention will also be explained shortly From the description of the invention which follows below, it will become apparent to one of skill in the art just how computer 40 should be programmed to perform its various functions in the practice of the invention.

Light source 22 is a near infrared source operating at a wavelength of about 850-plus-or-minus-about-30-nanometers, and light source 24 is a green source operating at a wavelength of about 540-plus-or-minus-about-30-nanometers. In the system, these two light sources are specifically operated, i.e., energized, under the control of computer 40 through control connections 44, 46, respectively. They are operated, one immediately after the other, preferably at a 50% duty cycle, and at a common light-output power level (i.e., at equal power levels). The common power level, established by computer 40, for these sources is that which is considered to be appropriate for illuminating, without harming, the limbus of the human eye, and so as to be certain produce the pattern of useful internal and output reflections which has been referred to above, and which will shortly be described in more detail below. Those skilled in the art will naturally and readily choose an appropriate power level according to their wishes, and to their selected operating environment and determined task, and accordingly, no specific power level is set forth herein.

As a side note at this point in the invention description, while, in system 10, the two light sources are operated at a common power level, they could be operated at different, respectively constantly maintained power levels so as to create not only this condition, but also the then associated condition of having a constant power-level differentiation. On a related point regarding the matter of light-source power level, in an application where, as suggested earlier herein, only a single light source is determined to be employed, this source would simply be operated at the appropriate constant power level.

In the embodiment of, and manner of practicing, the invention now being discussed, the above-mentioned light-source wavelengths have been chosen specifically to differentiate significantly the respective interactions (levels of "optical activity, or interactivity") which they experience with glucose, and specifically with the stated near infrared source wavelength being more optically active with glucose than the stated wavelength of the green source.

Light sources 22, 24 are deployed in system 10 orthogonally relative to one another, and effectively on opposite functional sides of previously mentioned, conventional beam combiner 26 which functions to "combine" the transmissions of light beams from the sources to establish a condition of incidence-light-transmission along a common incidence-illumination line, or path, shown by a dash-dot line 54 in the figures. The direction of illumination-light incidence is indicated by an arrow 56— this illumination passing through lens 28 which focuses the incident illumination at a spot location, or region, 14a adjacent the right side of limbus 14 as seen in FIG. 2 in the drawings.

The input end 34a in optical fibre 34 detects illumination from the two sources downstream from lens 28, as indicated in FIG. 1, and feeds this detected illumination in the direction indicated by an arrow 58, along an optical path shown by a dash-dot line 60, through previously mentioned lens 30 which focuses fibre-detected illumination onto photodiode 36. Information drawn from illumination thus received by photodiode 36 via the optical fibre is supplied through the previously mentioned (but not illustrated), associated signal amplifier and analogue-to-digital converter series circuit, and therefrom through data-flow connection line 48 as an input for and to computer 40.

As is illustrated in FIG. 2, incident illumination disposed along line 54 and which strikes limbus region 14a adjacent the right side of limbus 14 in this figure, initiates a pattern of cornea-based reflections, including a sub-pattern of multiple internal reflections, represented by a zigzag dashed line 62, and ultimately what is referred to herein as a resulting outbound reflection exiting the cornea adjacent its left side in the figure along a dash-dot line 64 in the direction indicated by an arrow 66.

While, as mentioned earlier herein, certain variations are possible in relation to the flow paths, or lines, along which incident and reflected illumination travels in the practice of the present invention, in system 10, lines 54, 64, each lie at an angle of 45° relative to line 20 which represents the line of sight of eye 12. As mentioned earlier, these angles are not illustrated with exactness in the drawing figures.

Reflection light disposed along reflection line 64, flowing in the direction of arrow 66, passes through previously mentioned lens 32 which creates a reflection image focused on photodiode 38. Information contained in this reflection illumination which is received by photodiode 38 is supplied through the previously mentioned (but not illustrated), associated signal amplifier and analogue-to-digital series circuit, and therefrom through data-flow connection line 50 to computer 40.

Considering now a typical operation of system 10, and the associated implementation of the methodology of the present invention, with specific reference, for illustration purposes, to glucose-concentration monitoring, computer 40 is initially appropriately programmed to handle all relevant computer-control and data-response and monitoring functions to be associated with practice of the invention methodology. Through the circuitry described above which connects the computer to light sources 22, 24 via control connection lines 44, 46, respectively, and by operation of the computer, these light sources are energized in a fashion whereby, in the particular practice of the methodology of the invention which will now be described, and as has been mentioned above as one preferred manner of operation, the light-output power levels of these two light sources are essentially equalized.

Beam combiner 26 combines the light beams generated by sources 22, 24—these beams being created in a 50% duty cycle, alternating fashion under the control of computer 40— and feeds the combined light beams toward and through lens 28 along common illumination-incidence line, or path, 54. On the "downstream" side of lens 28, the input end 34a of optical fiber 34, effectively, collects portions of these combined beams, and feeds collected, combined-beam information to its output end 34b which effectively sits at a focal point of lens 30, thus to create a related light-beam flow along path, or line, 60 through lens 30 to strike, at its other focal point, photodiode 36. Information/data relevant to what thus impinges photodiode 36 is supplied through data-flow connection line 48, and the previously mentioned, associated electronic circuitry, to computer 40, which, utilizing this information as feedback information, operates appropriately to control the energizations of sources 22, 20 or to achieve the power-output equalizations just mentioned above.

Recalling that light source 22 is a near infrared source, and that source 24 is a green source, it will be apparent that what results from energizing of these two sources is a combinational, alternating, red/green beam which flows along off-line-of-sight-axis-20 line 54, directed toward a focused spot which, with the system components properly positioned relative to a person's eye, such as eye 12, coincides with a fundus region, such as region 14a in fundus 14 of eye 12.

The focused, combinational beam, when it strikes a fundus region like region 14a, produces a pattern of reflections, such as the pattern shown in FIG. 2, including plural, eye-internal reflections like those represented by zigzag line 62, and a final, resulting outbound reflection, such as that shown by line 64. Because of the fact that the two, different, light-source wavelengths interact so differently with the eye property of aqueous glucose concentration, the outbound reflection will be characterized by reflection-intensity-level differences in the two components (infrared and green) of the out bound reflection beam flowing toward lens 32 along line 64.

Lens 32 focuses the outbound-reflection, combinational beam onto photodiode 38, data from which is then supplied by data-flow connection line 50, and the previously described electronic circuitry which is associated with that line, as another input for and to computer 40. Through appropriate calibration information developed and furnished to computer 40 respectively for different persons whose eye properties are to be examined and monitored, information acquired via a calibration-procedure which will be described shortly, computer 40, utilizing its appropriate algorithmic programming (mentioned earlier) will, in relation to the practice illustration now being presented, generate an output indication of blood-glucose concentration. This blood-glucose output information may be furnished to a user in a number of different well-known ways, including by presenting information on screen display 42.

Turning attention now to the issues of system alignment with respect to a person's eye, and to system calibration in a person-specific manner, it is, of course, important that system 10 be disposed relative to a person's eye to have a correct deployment disposition, such as that represented schematically in FIG. 1. As has been mentioned earlier herein, relative positioning established between the components of system 10 and a person's eye may be accomplished under computer control whereby computer 40 drives appropriate motors which multi-axially adjusts the positions of system components, which components may be supported, in any appropriate conventional manner, on a common framework. System adjustments during calibration will, of course, take place under circumstances where an eye to be examined/monitored is ultimately properly in place, in the sense that a person is ultimately appropriately seated and stabilized. However, at least initially, a person regarding whom calibration is to be performed, is placed in a near-correct position relative to the system elements. System adjustment then takes place, for example, by the presentation on screen display 42 of a spot of light respecting which the "examined" person is asked to focus his or her to-be-looked-at eye focused on that light spot. System positional adjustments are then made effectively to maximize outbound eye-reflection readings detected by photodiode 38.

It should be understood that, beyond the establishment of person-specific system calibration(s), each time that eye monitoring is to take place for an "eye-calibrated" person, system positional adjustment must be performed for that person.

While optional computer-driven automated positional adjustment has been mentioned, adjustment may also be entirely manual in nature if desired.

Concerning calibration, because the relevant physical properties of eyes may differ among persons, the system must be calibrated in a specific procedure performed for each person for whom monitoring is to take place. Such a procedure preferably involves, for each person to be "examined", the making of a conventional laboratory measurement to obtain a traditional blood glucose measurement value several times during a day, accompanied, in a manner which is as close to simultaneity as possible, by the performance of a reading-acquiring monitoring process using system 10, with the associated person, of course, positioned properly relative to the system-10 components. By this process, one can determine, and "fit", a curve which describes the relationship between system readings and, in the illustration now being given, blood-glucose concentration.

This curve is then entered into computer 40, and once entered, furnishes an appropriate, person-specific calibration for determining noninvasive blood glucose concentration for that person based upon system 10 readings. To be noted is the important fact that such person-specific calibration needs to be repeated at regular intervals, such as, for example, every six months. (Such a re-calibration frequency will typically be determined during clinical trials).

Once calibration is completed, and when it is "up-to-date" regarding a specific person, noninvasive, eye-property monitoring for that person is implemented simply as described above, with the person properly positioned for system performance.

As was mentioned earlier herein, one modified form of the invention methodology is one wherein a system constructed to implement it employs only a single light source, such as light source 22. Accordingly, looking now at FIG. 1 with this modification in mind, one should ignore the presences of light source 24 and of beam combiner 26 which would not be employed in such a modification. Light source 22 would, of course, be employed, and in the context of monitoring, glucose concentration, would be, as it is currently described, a near infrared source.

In this modified form of the invention, the light beam which is directed from source 22, along line 54, through lens 28 to limbus region 14a, is a single-wavelength beam, the source 22 for which could be operated by computer 40 either continuously or intermittently, as desired.

The effective feedback path earlier described with respect to obtaining light-flow intensity information on the downstream side of lens 28 by input end 34a in optical fiber 34 will continue to play a role in terms of furnishing computer 40 with information allowing this computer to control the operating light-output power level of singular source 22.

From this description of the just-outlined, single-source, modified form of the invention, and from a reading of the operational description given above regarding system 10 in a condition possessing two or more light sources, and the manner in which output-reflection information may be interpreted by computer 40 to present data reflecting glucose concentration, those skilled in the art will readily understand how to implement such a single-source form of the invention.

Accordingly, while preferred and best-mode manners of structuring and practicing the invention have been illustrated and described hereinabove, and a number of variations and modifications specifically mentioned, I appreciate that other variations and modifications will come to the minds of those skilled in the relevant art, and may be made in manners which will lie within the spirit and scope of the invention, and it is my intention that all such other variations and modifications will be understood to be embraced by the following claims to invention.

I claim:

1. An eye-property monitoring method comprising
in a seriatim manner, illuminating the eye from two or more, different-wavelength light sources whose respective wavelengths interact with internal eye properties in optically differentiated manners,
adjusting the operating levels of the sources to a predetermined relative setting,
by said illuminating, producing seriatim-light-source eye reflections including multiple internal reflections within the outer structure of the eye, and at least one resulting outbound reflection,
monitoring the outbound-reflection to detect therein the relative reflection levels associated with the sources, and
associating said detected, relative reflection levels with at least one eye property.

2. The method of claim 1 which further comprises (a) controlling the illuminating and adjusting steps with a computer, and (b) conducting the monitoring step with a computer.

3. The method of claim 1, wherein said illuminating is performed by directing light from the sources along a common illumination path which lies at an angle relative to the eye's line of sight.

4. The method of claim 1, wherein said producing is accomplished to effect eye reflections occurring within the cornea of the eye.

5. The method of claim 1, wherein said producing is conducted so as to effect eye reflections including reflections from the optical interface existing between the cornea and the aqueous humor of the eye.

6. A blood glucose monitoring method comprising
in an alternating manner, illuminating the eye from two, different-wavelength light sources, one of which has a wavelength to which glucose is more optically active than it is to the wavelength of the other source,
adjusting the operating levels of the two sources to a predetermined relative setting,
by said illuminating, producing eye reflections including multiple internal reflections within the outer structure of the eye, and at least one resulting outbound reflection, and
monitoring a at least one condition of the outbound reflection and determining blood glucose level therefrom.

7. The method of claim 6 which further comprises (a) controlling the illuminating and adjusting steps with a computer, and (b) conducting the monitoring step with a computer.

8. The method of claim 6, wherein said illuminating is performed by directing light from the two sources along a common illumination path which lies at an angle relative to the eye's line of sight.

9. The method of claim 6, wherein the two light sources are light-emitting diodes, and the two wavelengths are about 850- and about 540-nanometers.

10. The method of claim 6, wherein said alternating-manner illuminating is performed with a 50% duty cycle.

11. The method of claim 6, wherein said alternating is performed at a frequency of about 40Hz.

12. The method of claim 6, wherein said adjusting is performed to establish a constant, light-output-level relationship between the two sources.

13. The method of claim 6, wherein said producing is accomplished to effect eye reflections occurring within the cornea of the eye.

14. The method of claim 6, wherein said producing is conducted so as to effect eye reflections including reflections from the optical interface existing between the cornea and the aqueous humor of the eye.

15. An eye-property monitoring method comprising
illuminating the eye from at least one light source whose wavelength interacts with internal eye properties in an optically active manner,
controlling, to make substantially known and stable, at a predetermined setting, the operating-power/light-output level of the source,
by said illuminating, producing light-source eye reflections including (a) multiple internal reflections within the outer structure of the eye, and (b) at least one resulting outbound reflection,
monitoring the outbound-reflection to detect therein the reflection level associated with the at least one source, and
associating said detected reflection level with at least one certain eye property.

16. An eye-property monitoring system comprising
a light-source structure including a pair of light sources having different, respective wavelengths selected to interact with internal eye properties in optically differentiated manners, operable in a seriatim manner (a) to illuminate a person's eye, and (b) to produce, by such illumination, eye reflections including (1) multiple internal reflections within the outer structure of the eye, and (2) at least one resulting outbound reflection,
an optical monitoring structure operatively associated with said light-source structure, disposed for monitoring said a resulting outbound-reflection to detect therein the relative reflection levels associated with said sources, and
a result-determining structure operatively connected to said optical monitoring structure for associating said detected, relative, outbound reflection levels with an indication of at least one eye property.

17. The system of claim 16 [which further comprises] said light source structure configured to provide illumination along a common incidence illumination path[along which said light sources illuminate the eye].

18. The system of claim 16, wherein said result-determining structure is also operatively connected to said light-source structure, and comprises an appropriately programmed digital computer which is operable to establish the operating light-output levels of said light sources.

19. An blood glucose monitoring system comprising
a pair of light sources having different, respective wavelengths one of which is more optically active with respect to glucose than is the other, said sources being operable in a seriatim manner (a) to illuminate a person's eye, and (b) to produce, by such illumination, eye reflections including (1) multiple internal reflections within the outer structure of the eye, and (2) at least one resulting outbound reflection,
an optical monitoring structure operatively associated with said light-source structure, disposed for monitoring said resulting outbound-reflection to detect therein the relative reflection levels associated with said sources, and
a result-determining structure operatively connected to said optical monitoring structure for associating said detected, relative, outbound reflection levels with an indication of blood glucose level.

20. The system of claim 19 [which further comprises] said light source structure configured to provide illumination along a common incidence illumination path [along which said light sources illuminate the eye].

21. The system of claim 19, wherein said result-determining structure is also operatively connected to said light-source structure, and comprises an appropriately programmed digital computer which is operable to establish the operating light-output levels of said light sources.

22. An eye-property monitoring system comprising
at least one light source whose wavelength interacts with internal eye properties in an optically active manner, operable (a) to illuminate a person's eye, and (b) to produce, by such illumination, eye reflections including (1) multiple internal reflections within the outer structure of the eye, and (2) at least one resulting outbound reflection,
an optical monitoring structure operatively associated with said at least one light source, disposed for monitoring said resulting outbound-reflection to detect therein the reflection level associated with the at least one source, and
a result-determining structure, operatively connected to said optical monitoring structure for associating said detected, resulting reflection level with an indication of at least one eye property.

23. The system of claim 22 [which further comprises] said light source structure configured to provide illumination along a common incidence illumination path [along which said light sources illuminate the eye].

24. The system of claim 22, wherein said result-determining structure is also operatively connected to said at least one light source, and comprises an appropriately programmed digital computer which is operable to establish the operating light-output level of the source.

* * * * *